United States Patent
Reilly et al.

(10) Patent No.: US 7,060,991 B2
(45) Date of Patent: Jun. 13, 2006

(54) METHOD AND APPARATUS FOR THE PORTABLE IDENTIFICATION OF MATERIAL THICKNESS AND DEFECTS ALONG UNEVEN SURFACES USING SPATIALLY CONTROLLED HEAT APPLICATION

(76) Inventors: Thomas L. Reilly, 45 Chestnut St., Nutley, NJ (US) 07110; A. Ronald Jacobstein, 2370 NE. Ocean Blvd., Stuart, FL (US) 34996; K. Elliott Cramer, 12 roome Rd., Newport News, VA (US) 23601

( * ) Notice: Subject to any disclaimer, the term of this patent is extended or adjusted under 35 U.S.C. 154(b) by 139 days.

(21) Appl. No.: 10/410,605

(22) Filed: Apr. 10, 2003

(65) Prior Publication Data

US 2003/0230717 A1    Dec. 18, 2003

Related U.S. Application Data

(60) Provisional application No. 60/373,341, filed on Apr. 11, 2002.

(51) Int. Cl.
*G01N 25/72* (2006.01)

(52) U.S. Cl. .................. 250/443.1; 250/341.6

(58) Field of Classification Search ............. 250/443.1, 250/341.6, 341.1, 330, 332, 334, 358.1, 338.1, 250/339.02, 339.14, 338.3; 356/381, 237; 374/4

See application file for complete search history.

(56) References Cited

U.S. PATENT DOCUMENTS

| | | | |
|---|---|---|---|
| 3,629,584 A | 12/1971 | Blomgren, Jr. | |
| 3,790,362 A * | 2/1974 | Dahlberg et al. | 65/174 |
| 4,431,918 A | 2/1984 | White | |
| 4,609,820 A | 9/1986 | Miyamoto | |
| 4,647,220 A | 3/1987 | Adams et al. | |
| 4,826,326 A * | 5/1989 | Reynolds et al. | 374/5 |
| 4,914,299 A | 4/1990 | Jungkman et al. | |
| 4,988,210 A | 1/1991 | Koshihara et al. | |
| 5,292,195 A | 3/1994 | Crisman, Jr. | |
| 5,294,198 A | 3/1994 | Schlagheck | |
| 5,582,485 A * | 12/1996 | Lesniak | 374/5 |
| 5,711,603 A | 1/1998 | Ringermacher et al. | |
| 5,775,806 A | 7/1998 | Allred | |
| 6,000,844 A | 12/1999 | Cramer et al. | |
| 6,271,878 B1 | 8/2001 | Sera | |
| 6,394,646 B1 * | 5/2002 | Ringermacher et al. | 374/7 |
| 6,461,035 B1 | 10/2002 | Meinlschmidt et al. | |
| 6,593,574 B1 * | 7/2003 | Thomas et al. | 250/341.6 |
| 6,690,016 B1 * | 2/2004 | Watkins et al. | 250/341.7 |
| 6,751,342 B1 * | 6/2004 | Shepard | 382/141 |
| 6,759,659 B1 * | 7/2004 | Thomas et al. | 250/341.6 |
| 2002/0126732 A1 * | 9/2002 | Shakouri et al. | 374/130 |
| 2003/0169518 A1 * | 9/2003 | Irani | 359/820 |

* cited by examiner

*Primary Examiner*—Otilia Gabor
(74) *Attorney, Agent, or Firm*—Susanne M. Hopkins

(57) ABSTRACT

A method and apparatus for testing a material such as the water-wall tubes in boilers includes the use of a portable thermal line heater having radiation shields to control the amount of thermal radiation that reaches a thermal imager. A procedure corrects for variations in the initial temperature of the material being inspected. A method of calibrating the testing device to determine an equation relating thickness of the material to temperatures created by the thermal line heater uses empirical data derived from tests performed on test specimens for each material type, geometry, density, specific heat, speed at which the line heater is moved across the material and heat intensity.

22 Claims, 5 Drawing Sheets

| Tube 1 | Tube 2 | Tube 3 | Tube 4 | Tube 5 | Tube 6 |
|---|---|---|---|---|---|
| 1.59 x 2.86 x 0.38 | 1.27 x 4.45 x 0.38 | 0.95 x 4.76 x 0.38 | 0.95 x 2.22 x 0.38 | 0.64 x 3.81 x 0.38 | 0.64 x 0.64 x 0.19 |
| 1.59 x 3.49 x 0.38 | 1.59 x 1.59 x 0.19 | 1.27 x 1.27 x 0.19 | 0.95 x 3.18 x 0.38 | 0.64 x 4.45 x 0.38 | 0.64 x 1.27 x 0.19 |
| 1.59 x 4.13 x 0.38 | 1.59 x 2.22 x 0.19 | 1.27 x 1.91 x 0.19 | 0.95 x 3.49 x 0.38 | 0.64 x 5.08 x 0.38 | 0.64 x 1.91 x 0.19 |
| 1.90 x 1.91 x 0.19 | 1.59 x 2.86 x 0.19 | 1.27 x 2.54 x 0.19 | 0.95 x 4.13 x 0.38 | 0.95 x 0.95 x 0.19 | 0.64 x 2.54 x 0.19 |
| 1.90 x 2.54 x 0.19 | 1.59 x 3.49 x 0.19 | 1.27 x 3.18 x 0.19 | | 0.95 x 1.59 x 0.19 | 0.64 x 3.18 x 0.19 |
| 1.90 x 3.18 x 0.19 | 1.59 x 4.13 x 0.19 | 1.27 x 3.81 x 0.19 | | 0.95 x 2.22 x 0.19 | 0.64 x 3.81 x 0.19 |
| 1.90 x 3.81 x 0.19 | 1.59 x 1.59 x 0.38 | 1.27 x 4.45 x 0.19 | | 0.95 x 2.86 x 0.19 | 0.64 x 4.45 x 0.19 |
| 1.90 x 1.91 x 0.38 | 1.59 x 2.22 x 0.38 | 1.27 x 1.27 x 0.38 | | 0.95 x 3.49 x 0.19 | 0.64 x 5.08 x 0.19 |
| 1.90 x 2.54 x 0.38 | | 1.27 x 1.91 x 0.38 | | 0.95 x 4.13 x 0.19 | 0.64 x 0.64 x 0.38 |
| 1.90 x 3.18 x 0.38 | | 1.27 x 2.54 x 0.38 | | 0.95 x 4.76 x 0.19 | 0.64 x 1.27 x 0.38 |
| 1.90 x 3.81 x 0.38 | | 1.27 x 3.18 x 0.38 | | 0.95 x 0.95 x 0.38 | 0.64 x 1.91 x 0.38 |
| | | 1.27 x 3.81 x 0.38 | | 0.95 x 1.59 x 0.38 | 0.64 x 2.54 x 0.38 |
| | | | | | 0.64 x 3.18 x 0.38 |

US 7,060,991 B2

METHOD AND APPARATUS FOR THE PORTABLE IDENTIFICATION OF MATERIAL THICKNESS AND DEFECTS ALONG UNEVEN SURFACES USING SPATIALLY CONTROLLED HEAT APPLICATION

This application claims priority under 35 U.S.C. § 119 to U.S. Provisional Application No. 60/373,341 entitled METHOD AND APPARATUS FOR THE NON-DESTRUCTIVE IDENTIFICATION OF DEFECTS IN STRUCTURES HAVING CURVED SURFACES and filed on Apr. 11, 2002, the entire content of which is hereby incorporated by reference.

ORIGIN OF THE INVENTION

The invention described herein was jointly invented by inventors that include an employee of the United States Government and may be manufactured and used by or for the United States Government for United States Government purposes without payment of any royalties thereon or therefor.

FIELD OF THE INVENTION

This invention relates generally to non-destructive evaluation and particularly to the on-site detection and real time display of flaws or material loss in a structure having an uneven surface through the use of active thermography.

BACKGROUND OF THE INVENTION

Wall thinning due to corrosion in utility boiler water-wall tubing is a significant operational concern for boiler operators. Historically, conventional ultrasonics have been used for inspection of these tubes. However, ultrasonic inspection is very manpower intensive and a slow process. Therefore, thickness measurements are typically taken over a relatively small percentage of the total boiler wall and statistical analysis is used to determine the overall condition of the boiler tubing. Other inspection techniques such as electromagnetic acoustic transducer (EMAT), have been evaluated, however they provide only a qualitative evaluation by identifying areas or spots where corrosion has significantly reduced the wall thickness.

In U.S. Pat. No. 6,000,844, which is incorporated herein in its entirety by reference, a method and a portable apparatus are disclosed for the non-destructive identification of defects in structures. The apparatus includes a heat source and a thermal imager that move at a constant speed past a test surface of a structure. The thermal imager is offset at a predetermined distance from the heat source. The heat source induces a constant surface temperature, preferably along a continuously advancing line or narrow region on the material being tested. The imager follows the heat source and produces a video image of the thermal characteristics of the test surface. Material defects produce deviations from the constant surface temperature that move at the inverse of the constant speed. Thermal noise produces deviations that move at random speed. Computer averaging of the digitized thermal image data with respect to the constant speed minimizes noise and improves the signal of valid defects. The motion of thermographic equipment coupled with a high signal-to-noise ratio renders it suitable for portable, on-site analysis.

SUMMARY OF THE INVENTION

A system and method for testing a material according to an embodiment of the invention includes directing thermal radiation onto the material to heat the material above ambient temperature, preferably along a continuously advancing line or narrow region of the material, moving the thermal radiation along the material in a direction at a constant rate with respect to the material, and thermally imaging the material to create a plurality of thermal images. In one embodiment of the invention, a radiation shield used in conjunction with a line heater that produces the thermal radiation prevents stray radiation from adversely affecting the readings taken by the thermal imager. A benefit of using the radiation shield with a line heater is that a first portion of a thermal image collected can be obtained from a first portion of the material ahead of the thermal radiation in the direction of movement of the line heater, and a second portion of the thermal image collected can be obtained from a second portion of the material behind the thermal radiation in the direction of movement of the heater.

A problem encountered when attempting to detect and measure areas of material loss in water-wall tubing inside boilers is the need for a rapid, large area measurement device. Water-wall tubing inside boilers typically includes a series of small radius of curvature tubes that are either freestanding side-by-side or welded together with webbing material. The inspection area inside a boiler can also be very large with typical boilers having walls that may measure 30 ft wide×30 ft long×150 ft high. Therefore, any inspection system must be capable of inspecting the small tubes over very large areas in a rapid fashion.

A thermal line scanner such as disclosed in U.S. Pat. No. 6,000,844, provides an effective technique for the inspection of flat, or nearly flat structures and the extraction of thickness measurements from the infrared data. Additional problems are encountered, however, when attempting to implement similar procedures for testing structures and materials having a small radius of curvature such as the tubing found in fossil fuel boilers. Because of the small radius of curvature, it is difficult to uniformly apply heat from the line source and therefore heat flow occurs not only through the thickness of the material but also circumferentially around the tubes. If data could be collected very close to the heat source this effect would be minimized, but in practical application this is difficult to do and therefore must be accounted for in the analysis of the resulting temperature signature. Additionally, because a surface made up of a series of tubes does not provide an inspection surface that is at a uniform distance from a line heater such as a quartz lamp, light from the lamp can leak out around the edges of the lamp and can be scattered into the infrared imager used for data acquisition. This scattered light can result in saturation of the detectors of the imager and thus produces false temperature readings.

A large variation in the initial temperature of the target structure can also lead to errors in measuring the thickness through thermal imaging, and therefore a method according to an embodiment of the invention dynamically subtracts the background temperature from the heated temperature that results as the line heater is passed over the surface.

DESCRIPTION OF THE PREFERRED EMBODIMENTS

Figure 2:
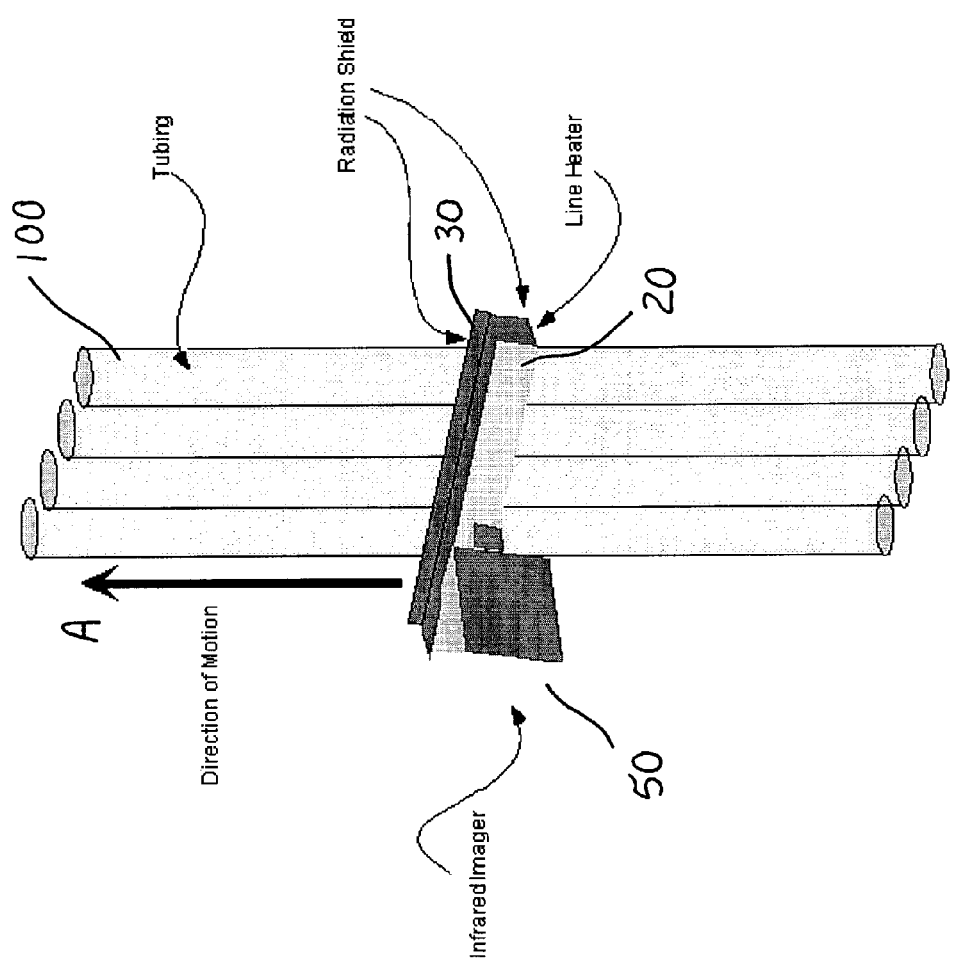
FIG. 2 is a schematic diagram of an infrared camera, heat source and radiation shield, as they would be configured while performing an inspection of a series of tubes.

FIG. 2 shows a schematic diagram of an infrared camera 50, heat source 20, and radiation shield 30, as they would be configured while performing an inspection of a series of tubes 100 using a system and method according to an embodiment of the invention. The infrared camera 50 produces a series of frames of data as the infrared camera and line heater 20 are moved in the direction designated with arrow A along tubing 100. Each frame of data produced by the infrared camera 50 contains several lines of temperature information recorded in front of the line heater 20 and a larger portion of lines of temperature information recorded behind the line heater 20 as viewed in the direction of arrow A. Each line of temperature information is a series of pixels on a thermal image produced by the infrared camera 50.

Figure 1:
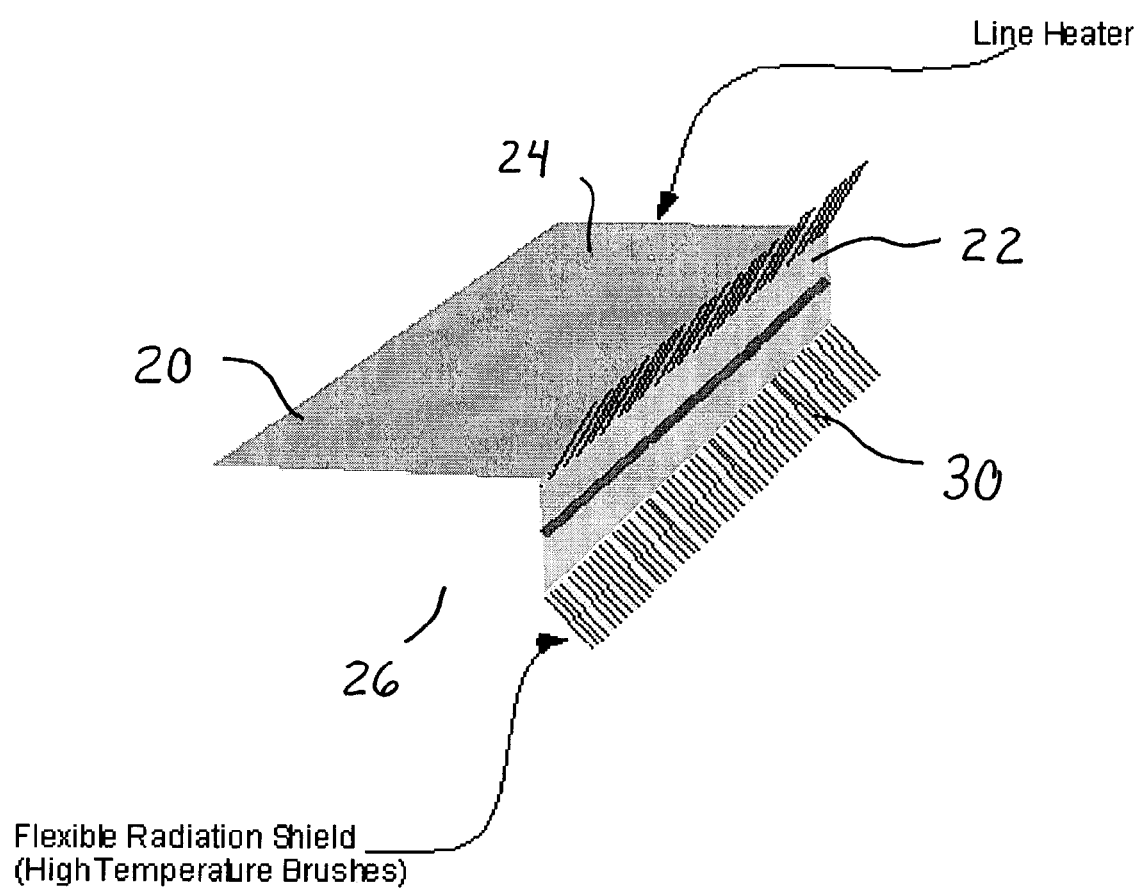
FIG. 1 shows a line heater with a flexible radiation shield.

As shown in FIG. 1, a flexible radiation shield 30 is provided in accordance with an embodiment of the invention to include two high temperature brushes that extend from the front edge of the line heater 30 at both a top surface 24 and a bottom surface 26 of the line heater 20. When the line heater 20 is positioned adjacent tubing 100 as shown in FIG. 2, and moved in the direction of arrow A along the tubing, the radiation shield 30 slightly drags the surface of the tubing 100 and keeps any stray radiation produced by the line heater 20 from being reflected into the infrared camera 50. The flexibility of this radiation shield 30 allows the device to accommodate uneven surfaces such as boiler tubing while keeping all of the applied heat directed toward the surface. The distance that the brushes, which make up radiation shield 30, extend from the front edge 22 of line heater 20 can be adjusted as the line heater 20 is adjusted in position relative to the surface of tubing 100.

The radiation shield 30 allows the infrared camera 50 to be positioned so that a portion of the thermal image collected is focused before the heat from line heater 20 is applied to the structure being inspected. Without the radiation shield in place, the uneven surface presented by e.g. a series of parallel tubes could result in scattered thermal radiation saturating the detectors of the imager, and thereby affecting the accuracy of the test results. Since the entire device is translated at a constant speed in the direction of motion A over the surface of the tubing 100, the portion of the image collected before the material at a particular location is heated can then be used as a background and subtracted from the measured temperature at the same location once heating has occurred. This method corrects for variations in the initial temperature of the structure being inspected.

A method according to an embodiment of the present invention calibrates and effectively extracts thickness information from the acquired data when inspecting surfaces with a small radius of curvature such as the water-wall tubing within boilers. The thermal line scanner described in U.S. Pat. No. 6,000,844 indicates that the thickness of a structure being inspected is inversely proportional to the temperature measured. An assumption made in U.S. Pat. No. 6,000,844 is that the test article is a semi-infinite flat plate, which is not the case with boiler tubes or other curved structures.

In accordance with an embodiment of the present invention, an equation of the form:

$L=aT^{-b}$ relates the thickness L of the material to the temperature $T$ measured where: (1)

$a=q/(v*\rho*c)$ (2)

where q=total energy put in by the line heater,
v=velocity at which the line heater is moved along the material,
$\rho$=density of the material, and
c=specific heat of the material.

The exponent (−b) would be −1 in the case where the material being tested is a semi-infinite flat plate, but will be different from −1 where the material being tested has a small radius of curvature such as with the series of water-wall tubes in a boiler. Accordingly, the exponent (−b) in equation (1) above is a function of the geometry of the surface being tested, and can be determined empirically by performing a calibration test on a sample of material having the same geometry, density and specific heat, and by performing the calibration test using the same test set-up including the speed at which the line heater is moved along the surface and the total amount of energy being put in to the surface.

Figure 3:
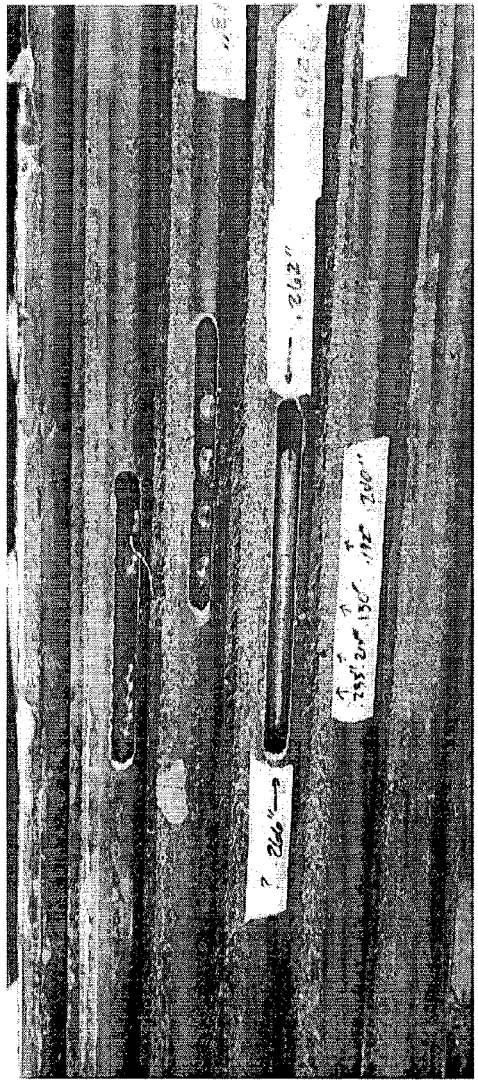
FIG. 3 shows a picture of a specimen fabricated from typical boiler tube material and having a number of regions with reduced thickness, along with a table of the sizes of the regions having reduced thickness material in cm.

In a method according to an embodiment of the present invention, a calibration specimen is fabricated from typical boiler tube material, where the thickness of a number of regions is reduced in a controlled manner by machining. FIG. 3 shows a picture of this specimen along with a table of the sizes of the controlled material loss regions that have been machined into the specimen. Data for this test specimen is acquired using a line heater 20 and thermal imager 50 arranged as shown in FIG. 2 and including a radiation shield 30 extending from the front edge of the line heater 20 and contacting tubing 100 as the line heater 20 and thermal imager 50 are moved in the direction A along the tubing 100.

The temperatures at a series of distances behind the line heater 20 are acquired during the testing of the specimen. For each distance behind the line heater 20, the temperature of each average region at that location on the sample as determined from the thermal images produced by infrared camera 50, is used to calculate a thickness using equation (1) above, with (b) being selected from a number of values ranging from 1.0 to 1.25. As discussed above, in a scenario where the test specimen is a semi-infinite flat plate, and the thermal image could be taken very close to the point at which heat is being applied to the material, the thickness at that point would be inversely proportional to the temperature as related by the equation $L=aT^{-1}$ However, when measuring thickness using a thermal imager on an uneven surface such as the tubing in a boiler, and under practical constraints that prevent the thermal image from being taken exactly at the point where heat is applied, the exponent (−b) in equation (1) above varies from −1.

Figure 4:
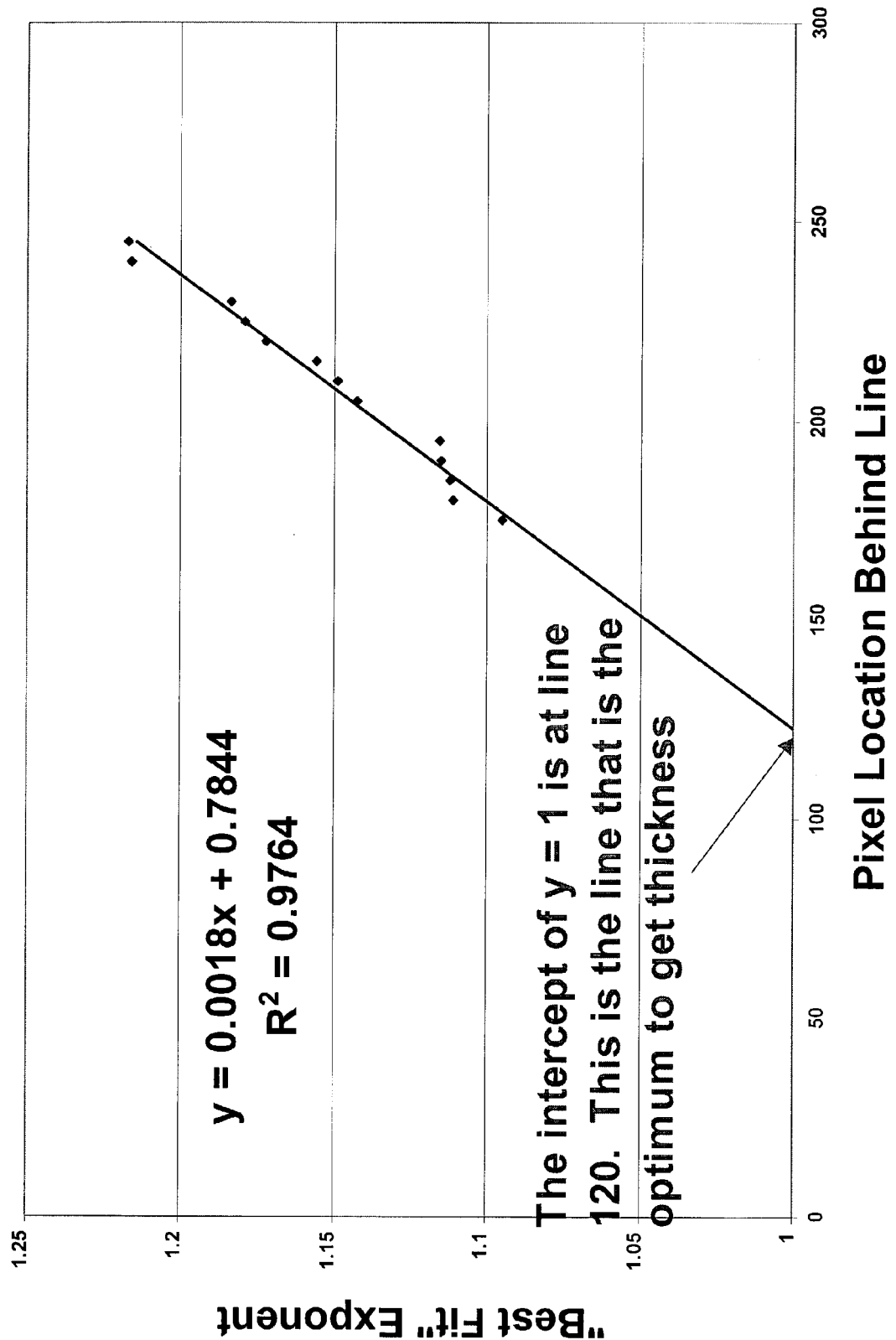
FIG. 4 is a plot of the exponent in an equation relating thickness of material to measured temperature of the material versus the distance behind the line heater where the thickness and temperature are measured.

FIG. 4 shows a plot of (b) versus the distance behind the line heater 20 measured in pixels. From this data, the changes in (b) appear to be linear with distance from the heater, and the point where (b) would be 1 (the exponent (−b)=−1) can be extrapolated. As shown in FIG. 4, (b)=1 at line 120 (where 120 is the number of pixels on the thermal image), which is approximately 1.0 inch behind the line of heat created by line heater 20. It is not possible to measure the temperature at this distance behind the line heater 20 since the infrared imager 50 does not have a direct line of sight with that point. Accordingly, the thickness can be calculated at any distance behind the heater 20 from equation (1) by using the exponent (−b) that has been determined from the data of FIG. 4 and calculating the coefficient (a) based on one area of known thickness using equation (2) above. Once this is done, equation (1) above will provide the thickness of the curved surface at any given point.

In accordance with an embodiment of the invention, the calibration curve of FIG. 4 is determined for each particular material type, geometry, speed and heat intensity. Therefore, to calculate thickness for an unknown material, a calibration specimen of that material is created in the geometry of interest with a series of known defects that can be used to produce a calibration curve similar to FIG. 4. Once this is done, the specific exponent (−b) determined and any point of known thickness on the structure under inspection can be used to calculate the thickness for all other points on the structure under the given inspection conditions including speed, geometry, etc.

Figure 5B:
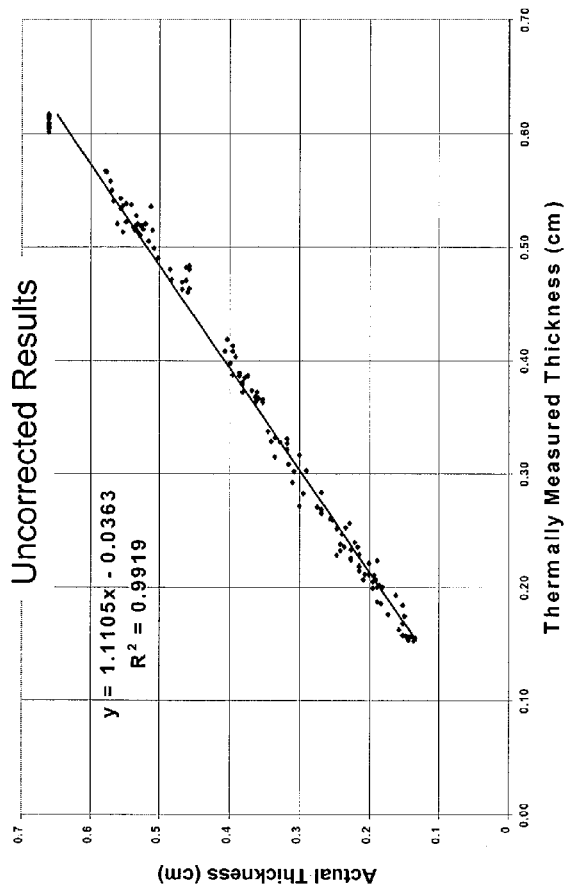
FIG. 5B shows a graph similar to the graph in FIG. 5B, but where the deviation between actual thickness of the material and thickness measured with a thermal line scanner is approximately 11% (as illustrated by the slope of 1.1105.)
Figure 5A:
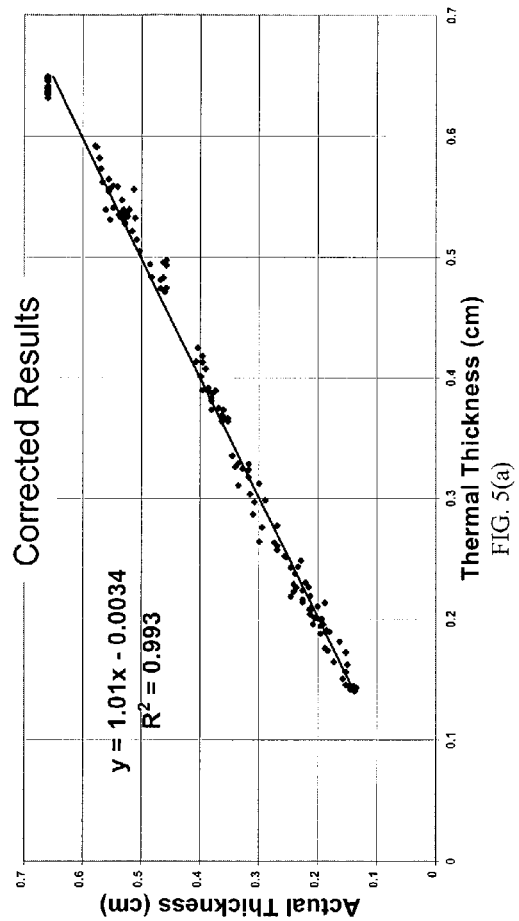
FIG. 5A shows a graph of actual thickness of a material versus thickness determined by measuring with a thermal line scanner where the deviation is approximately 1% (as illustrated by the slope of 1.01.)

FIG. 5A shows a plot of actual thickness of a specimen versus thickness as determined from a temperature measured by the infrared camera 50 and calculations according to equations (1) and (2) above, where (b) is selected as 1.09. As illustrated by the equation of the line through the data points, the slope of the line is 1.01, which indicates a 1% deviation between actual thickness and measured thickness. The $R^2$ value in FIGS. 4, 5a and 5b is the square of the residual of the straight line fit of the data. The residual is the vertical difference between the data at each point and the straight line that best fits the data. In calculating the straight line fit, an iterative process is performed, such as by using a computer, to find a line where this squared residual is as small as possible (this gives rise to what is called a least squares curve fit). After finding the least squares fit for the plot of the data, the computer normalizes the squared residual (dividing by the total number of points on the curve). Therefore, the closer that $R^2$ is to 1, the better the fit of the straight line through the plot of the data. The least squares fit of the data to the line shown in FIG. 5A is represented by $R^2=0.993$.

FIG. 5B shows a plot of actual thickness of the specimen versus thickness as determined from a temperature measured by the infrared camera 50 and calculations according to equations (1) and (2) above, where (b) is selected as 1. As illustrated by the equation of the line through the data points, the slope of the line is 1.1105, which indicates an 11% deviation between actual thickness and measured thickness. The least squares fit of the data to the line shown in FIG. 5B is represented by $R^2=0.9919$.

A number of different materials can be used for the radiation shield 30 illustrated in FIG. 1. Rubber cut to an appropriate length can be used and shaped to conform to the surface of the structure being inspected. Where the surface is relatively uniform, plexiglass is another material suitable for a radiation shield since it is transparent at visible wavelengths of light, but opaque to infrared wavelengths.

In an alternative method according to an embodiment of the invention, the inspection before the heat source which is used as a means for performing a background correction is eliminated and replaced with two successive scans, one with the heater on and one with it off, the determined values being directly subtracted one from the other. Additionally, in a further alternative embodiment of the invention, instead of directly looking at the object to measure the temperature before and after the heating, a mirror, or series of mirrors, is used to allow imaging before and after the heat source. These mirrors are also used to select only the areas of interest and discard the remainder of the data.

What is claimed is:

1. A method of testing a material comprising:
   directing thermal radiation onto the material to heat the material above ambient;
   moving the thermal radiation along the material in a direction at a constant rate with respect to the material; and
   thermally imaging the material to create a plurality of thermal images with a first portion of an image collected being obtained from a first portion of the material ahead of said thermal radiation in said direction, and a second portion of the image collected being obtained from a second portion of the material behind said thermal radiation in said direction.

2. The method according to claim 1, wherein said plurality of thermal images are collected as said thermal radiation is moved along said material, each of said thermal images having said first and second portions.

3. The method according to claim 2, wherein an initial temperature of said first portion of the material is determined from said first portion of one of said thermal images, a heated temperature of said first portion of the material is determined from said second portion of another one of said thermal images, and said initial temperature is subtracted from said heated temperature.

4. The method according to claim 3, wherein said initial temperature and heated temperature are determined for a plurality of positions along said material, said initial temperatures are subtracted from said heated temperatures to calculate adjusted temperatures at each of said positions, and
   actual thickness of said material is measured at each of said plurality of positions.

5. The method according to claim 4, wherein said adjusted temperatures are calculated for a series of distances behind said thermal radiation with respect to said direction of movement of said thermal radiation.

6. The method according to claim 5, wherein said adjusted temperatures (T) are related to thicknesses (L) of said material at each of said series of distances behind said thermal radiation by a first equation:

$L=aT^{-b}$, wherein a is a function of total energy (q) put into said material by said thermal radiation, the speed (v) at which said thermal radiation is moved along said material, the density (p) of the material and the specific heat (c) of the material in accordance with a second equation: $a=q/(v*p*c)$; and b is determined by substituting actual measured thicknesses of a test specimen of said material and said adjusted temperatures at a plurality of points into said first equation.

7. The method according to claim 1,
   wherein the thermal radiation is produced with a line heater and the thermal images are produced by an infrared camera.

8. The method according to claim 7, wherein the line heater includes a radiation shield that controls scatter of the thermal radiation directed onto the material.

9. The method according to claim 8, wherein the radiation shield comprises flexible brushes that extend from a front edge of the line heater and make contact with the material.

10. The method according to claim 1, wherein an initial temperature of said first portion of the material, is determined from said first portion of one of said thermal images, a heated temperature of said first portion of the material is determined from said second portion of another one of said thermal images, and said initial temperature is subtracted from said heated temperature to determine an adjusted temperature for said first portion of the material.

11. The method according to claim 10, wherein said material is a test specimen having a plurality of regions of reduced thickness, said method further including measuring the thicknesses at each of said plurality of regions of reduced thickness, creating thermal images of each of said plurality of regions and determining said adjusted temperatures at each of said plurality of regions.

12. The method according to claim 11, wherein said adjusted temperatures (T) are related to said measured thicknesses (L) of said test specimen at each of said plurality of regions by a first equation:

$L=aT^{-b}$, wherein (a) is a function of total energy (q) put into said material by said thermal radiation, the speed (v) at which said thermal radiation is moved along said material, the density (p) of the material and the specific heat (c) of the material in accordance with a second equation: a=q/(v*p*c).

13. The method according to claim 12, wherein the exponent (b) is calculated from said first equation for said test specimen.

14. The method according to claim 13, further including determining thicknesses (L) of a boiler wall made from said material at a plurality of regions on said boiler wall from said first and second equations using the same value of (a) as used for said test specimen, adjusted temperatures (T) determined from thermal images taken of said plurality of regions, and said exponent (−b) for said test specimen, and calculating said thicknesses of said boiler wall from the equation:

$L=aT^{-b}$.

15. A meted of testing a material comprising:
thermally imaging a plurality of different regions on the material, before the material is heated, to create a plurality of different background thermal images;
directing thermal radiation onto the material to heat the material to a temperature above ambient;
moving the thermal radiation along the material in a direction at a constant rate with respect to the material;
thermally imaging each different region of the plurality of different regions on the heated material to create a plurality of different thermal images of heated regions each thermal image corresponding to a respective background thermal image; and
subtracting a temperature determined from a background thermal image for a region from the temperature determined from a corresponding thermal image for that heated region, to obtain an adjusted temperature for each of the plurality of different regions.

16. The method according to claim 15, wherein the adjusted temperature (T) is related to thicknesses (L) of the material at each of the plurality of different regions by a first equation:

$L=aT^{-b}$, wherein a is a function of total energy (q) put into the material by the thermal radiation, the speed (v) at which said the thermal radiation is moved along the material, the density (p) of the material and the specific heat (c) of the material in accordance with a second equation: a=q/(v*p*c); and
b is determined by substituting actual measured thicknesses of a test specimen of the material and the adjusted temperatures at a plurality of points into the first equation.

17. An apparatus for testing a material, comprising:
a heater mounted for movement relative to said material;
a thermal imager mounted in fixed relationship to said heater and adapted to take thermal images of said material; and
a thermal radiation shield positioned to control the amount of thermal radiation from said heater that can enter said thermal imager, wherein said thermal imager and said heater in said fixed relationship are adapted to collect a first portion of an image obtained from a first portion of the material ahead of the thermal radiation, and to collect a second portion of the image obtained from a second portion of the material which is behind the thermal radiation.

18. The apparatus according to claim 17, wherein said thermal radiation shield comprises flexible flanges extending from a front edge of said heater.

19. The apparatus according to claim 18, wherein said flexible flanges comprise brushes.

20. An apparatus for testing a material, comprising:
means for directing thermal radiation onto the material to heat the material above ambient;
means for moving the thermal radiation along the material in a direction at a constant rate with respect to the material; and
means for thermally imaging the material to create a plurality of thermal images, wherein said means for thermally imaging is mounted in a fixed relationship to said means for moving the thermal radiation, and said means for moving the thermal radiation and said means for thermally imaging are adapted to collect a first portion of an image obtained from a first portion of the material ahead of the thermal radiation in said direction, and to collect a second portion of the image obtained from a second portion of the material behind the thermal radiation in said direction.

21. The apparatus according to claim 20, wherein:
said means for directing said thermal radiation onto said material comprises a thermal radiation shield positioned to control the amount of thermal radiation from said means for directing thermal radiation that can enter said means for thermally imaging said material.

22. An apparatus for testing a material, comprising:
means for directing thermal radiation onto the material to heat the material above ambient;
means for moving the thermal radiation along the material in a direction at a constant rate with respect to the material;
means for thermally imaging the material to create a plurality of thermal images; and
said means for directing said thermal radiation onto said material comprising a thermal radiation shield positioned to control the amount of thermal radiation from said means for directing thermal radiation that can enter said means for thermally imaging said material, wherein said means for thermally imaging is in a fixed relationship with said means for moving the thermal radiation, and said means for thermally imaging and said means for moving the thermal radiation are adapted to collect a first portion of an image obtained from a first portion of the material ahead of the thermal radiation in said direction, and to collect a second portion of the image obtained from a second portion of the material which is behind the thermal radiation in said direction.

* * * * *